United States Patent [19]

Zeikus et al.

[11] 4,430,429
[45] Feb. 7, 1984

[54] PRODUCTION OF VITAMIN $B_{12}$-ACTIVITY SUBSTANCES

[75] Inventors: Joseph G. Zeikus; Joseph A. Krzycki, both of Madison, Wis.

[73] Assignee: Wisconsin Alumni Research Foundation, Madison, Wis.

[21] Appl. No.: 286,247

[22] Filed: Jul. 23, 1981

[51] Int. Cl.³ .................. C12P 19/42; C12N 1/32; C12N 1/20; C12R 1/01
[52] U.S. Cl. ................... 435/86; 435/247; 435/253; 435/822
[58] Field of Search ............ 435/86, 247, 822, 253

[56] References Cited

U.S. PATENT DOCUMENTS

| | | | |
|---|---|---|---|
| 2,703,302 | 3/1955 | Rickes et al. | 435/86 X |
| 3,018,225 | 1/1962 | Long | 435/86 |
| 3,964,971 | 6/1976 | Johan et al. | 435/86 X |
| 3,979,259 | 9/1976 | Johan et al. | 435/86 |
| 4,106,988 | 8/1978 | Ohsugi et al. | 435/247 |
| 4,119,492 | 10/1978 | Kojima et al. | 435/247 X |

FOREIGN PATENT DOCUMENTS

| | | | |
|---|---|---|---|
| 55-96091 | 7/1980 | Japan | 435/86 |
| 56-11438 | 3/1981 | Japan | 435/86 |
| 2042548 | 9/1980 | United Kingdom | 435/86 |

OTHER PUBLICATIONS

J. G. Zeikus et al., Current Microbiology, vol. 3, pp. 381–386; 1980.
J. Krzycki et al., Current Microbiology, vol. 3, pp. 243–245; 1980.
American Type Culture Collection Catalogue of Strains I, Fifteenth Edition pp. 92 and 140; 1982.

*Primary Examiner*—Robert J. Warden
*Attorney, Agent, or Firm*—Quarles & Brady

[57] ABSTRACT

Vitamin $B_{12}$-active substances are produced by the fermentation of an aqueous medium consisting essentially of methanol as the main source of assimilable carbon, a source of assimilable nitrogen, cobalt ions and essential growth factors and minerals with a vitamin $B_{12}$-activity substance producing organism capable of growing under anaerobic conditions.

9 Claims, No Drawings

PRODUCTION OF VITAMIN B₁₂-ACTIVITY SUBSTANCES

FIELD OF THE INVENTION

The present invention relates to the preparation of vitamin $B_{12}$. More particularly, it relates to the preparation of substances having vitamin $B_{12}$ activity by fermentation on media containing methanol as the main source of assimilable carbon and energy.

BACKGROUND OF THE INVENTION

Vitamin $B_{12}$ has been prepared synthetically but the process is prohibitively expensive.

In U.S. Pat. No. 2,703,302, it is disclosed that vitamin $B_{12}$-active substances may be produced by fermentation utilizing selected vitamin $B_{12}$-active substance producing strains of microorganisms of the genus Alcaligenes, the genus Bacillus, the genus Escherichia, the genus Mycobacterium, the genus Pseudomonas and the genus Streptomyces.

An improved fermentation process for the preparation of substances having vitamin $B_{12}$-activity by fermentation using *Pseudomonas denitrificans* is disclosed in U.S. Pat. No. 3,018,225. The process is said to produce vitamin $B_{12}$-active substances in high yield at a rapid rate and without the significant production of undesirables such as antibiotics.

The currently employed commercial process for producing vitamin $B_{12}$ by fermentation on carbohydrate media employs highly selected strains of microorganisms such as *Proionobacterium shermanii* or Streptomyces species. Obviously, it would be advantageous to be able to produce vitamin $B_{12}$ commercially employing less expensive non-carbohydrate media.

SUMMARY OF THE PRESENT INVENTION

It is the primary object of the present invention to disclose a process of preparing vitamin $B_{12}$ by fermentation employing less expensive media than the carbohydrate substrates currently used.

In the present invention, vitamin $B_{12}$-activity substances are produced by the anaerobic fermentation of nutrient media containing methanol as the primary source of carbon and energy. The fermentation is preferably conducted employing either *Methanosarcina barkeri* or *Butyribacterium methylotrophicum* as the producing organism.

DESCRIPTION OF THE PREFERRED EMBODIMENT

The fermentation procedure of the present invention is preferably conducted by inoculating an aqueous nutrient medium containing methanol as the main source of assimilable carbon and energy, a source of assimilable nitrogen and essential growth factors and minerals, including cobalt ions, with a vitamin $B_{12}$-activity substance producing strain of *Methanosarcina barkeri* or *Butyribacterium methylotrophicum* and conducting the fermentation under anaerobic conditions.

Methanol is an excellent substrate for vitamin $B_{12}$ synthesis as it is inexpensive, soluble, renewable and relatively stable.

The MS strain of *Methanosarcina barkeri* which is to be employed has been deposited on an unrestricted basis in the Deutsch Sommlung von Mikroorganism (DSM) Collection in Gottingen, Federal Republic of Germany and assigned German culture accession number D 800.

The *Methanosarcina barkeri* microorganism employed exhibits the characteristics of this organism described by Weimer, P. J. and Zeikus, J. C. 1978, *Arch. Microbiol* 119:49–57.

During the growth of *M. barkeri* the cells must be protected from even occasional exposure to light since this can reduce the yield by a factor of two. In addition, complex, undefined, organic materials such as yeast extract or trypticase should be excluded from the medium in order to obtain optimal $B_{12}$ yields.

The nutrient medium utilized for *M. barkeri* growth should contain, in addition to the source of assimilable carbon, a source of assimilable nitrogen, a source of cobalt ions and various mineral salts to supply the tracer mineral requirements of the bacterium. The medium is sterilized by heating prior to inoculation.

The amount of methanol which can be present in the medium must be a non-toxic amount which with *M. barkeri* MS 800 is up to about 1%. However, it is to be understood that selected strains or mutants that are able to grow on higher concentrations of methanol can also be employed and are intended to be within the scope of the present invention.

Inorganic nitrogen derivatives are preferably used as the source of assimilable nitrogen as, for example, inorganic ammonium compounds, such as ammonium hydroxide, ammonium phosphate, ammonium sulfate and other ammonium salts. A concentration of a source of assimilable nitrogen of about 0.1% by weight of the nutrient medium ordinarily results in good yields, however a range of concentrations may be employed depending on the characteristics of the nitrogen-containing compounds.

Mineral nutrients are necessary in the medium to obtain good production of vitamin $B_{12}$-active substances. It is desirable to add salts containing the elements of potassium, sulphur and phosphorous. The following minerals also are apparently required in tract amounts (from about 1 to about 100 p.p.m. of each): zinc, iron, manganese and magnesium. It is necessary, of course, that the medium contain a nontoxic amount of cobalt ions in the range of about 1 to 50 p.p.m., and preferably 1 to 10 p.p.m. The cobalt and trace elements can be added by adding suitable salts such as the chlorines, sulphates, and the like.

The fermentation procedure utilizing *Methanosarcina barkeri* is ordinarily carried out by means of submerged growth with agitation under anaerobic conditions preferably in the absence of light. The fermentation is conducted at a temperature within the range of 25° C. to 42° C. and it is preferred to utilize a temperature within the range of 35° C. to 40° C., the preferred temperature being about 37° C. Under these preferred fermentation conditions, it has been found that the maximum concentration of vitamin $B_{12}$-active substances is present after a fermentation period within the range of about 40 to 60 hours.

The fermentation may be carried out over a fairly broad range of hydrogen ion concentration. The pH of the starting medium is preferably adjusted to a range of 7.0 to 7.4 to achieve optimum results. The operative pH range is from 6.5 to 8.5.

Even with *M. barkeri* MS which is a non-optimized strain, the *M. barkeri* produces more $B_{12}$ per unit cell (i.e. >1% cell dry weight is $B_{12}$) than other described organisms. It is anticipated that with a strain optimized for $B_{12}$ production and an optimized medium, production by *M. barkeri* will far exceed the per liter production levels of the Propioni bacterium optimized strain. An increase in cell mass produced per liter will also increase $B_{12}$ yields. *M. barkeri* normally ceases growth before the exhaustion of substrate. However, media optimization may prevent this so that cell yields per liter can significantly increase.

The other preferred Vitamin $B_{12}$-active substance producing organism is *Butyribacterium methylotrophicum* which is a methylotrophic, acidogenic, anaerobic bacterium that was first isolated from a sewage digestor in Marburg, Federal Republic of Germany.

The neotype strain of the species is a pure culture of the Marburg strain which has been deposited on an unrestricted basis in the American Type Culture Collection (Rockville, Md.) accession number ATCC 33266. It is a mesophilic, Gram-positive, nonmotile, pleomorphic rod that performs homoacetic, homobutyric, or heteroacidic fermentations. Cell morphology varies from single or paired straight rods to rudimentary branched rods, club-shaped cells, or oval refractile cells. Cell heat resistance correlated with the presence of a few refractile cells. Electron micrographs of thin sections revealed a thick monolayered cell wall and an atypical spore structure. The DNA base composition was 48.8±0.2 mol% guanosine plus cytosine. Corrinoid levels varied from 0.35±0.16 to 7.9+1.6 mg/g cell dry weight when cells were grown on glucose or methanol, respectively. Batch growth in a mineral medium that contained 0.1% yeast extract, $N_2/CO_2$, 100 mM methanol, and 50 mM Na acetate displayed a 20 h doubling time, final $A_{540}$ of 0.9, butyric acid yield of 25 mM, and stoichiometry of 3 mol butyrate formed per 10 mol methanol fermented. The isolation and characterization of the Marburg strain is described in detail by Zeikus et al in *Current Microbiology*, Vol. 3 (1980) pp. 381–386 which is incorporated by reference herein.

When *B. methylotrophicum* is the producing microorganism the nutrient medium is supplemented with yeast extract or a growth factor from yeast extract (less than 0.2% of media) and maximum cell growth is obtained when the media also contains a high concentration of acetate (at least 0.1%) as a growth stimulator.

Although *B. methylotrophicum* will grow on CO to produce cells and acetic acid, the presence of CO is to be avoided for maximum Vitamin $B_{12}$-activity substance production.

The fermentation broths obtained by the practice of the present invention using either of the preferred producing organisms contain the vitamin $B_{12}$-active substances substantially uncontaminated with undesired by-products such as antibiotics.

The term "vitamin $B_{12}$-active substances" as used herein includes both vitamin $B_{12}$ and the vitamin $B_{12}$-like substances which are sometimes called vitamin $B_{12}$ analogs. These vitamin $B_{12}$-like substances are characterized by their ability to be readily convertible into vitamin $B_{12}$ by treatment with cyanide ion (See U.S. Pat. No. 2,530,416) and/or which contain a corrin ring system and are utilizable by *E. coli* 113-3 as a replacement for vitamin $B_{12}$.

The vitamin $B_{12}$-active substances produced in accordance with the present invention since they are free of undesired products and are suitable, without the need for involved purification treatments, for use as concentrates having antipernicious activity and as feed supplement. Thus, a fermentation broth or the concentrate prepared therefrom can be used directly without purification to enrich animal feeds deficient in the animal proteins, as, for example, feeds consisting of edible vegetable protein matter.

When it is desired to recover a purified vitamin $B_{12}$-active substance concentrate or pure vitamin $B_{12}$ from the fermentation broth, this can be accomplished by conventional purification techniques, e.g. chromatography and crystallization from solvents.

The practice of the present invention is further illustrated by the examples which follow:

EXAMPLE 1

*Methanosarcina barkeri* Growth on Methanol

A medium of the following composition was prepared.

| Constituent | g/l Dist. H O |
|---|---|
| NaCl | 0.9 |
| $MgCl.6H_2O$ | 0.2 |
| $CaCl_2.2H_2O$ | 0.1 |
| $NH_4Cl$ | 1.0 |
| $KH_2PO_4$ | 1.5 |
| $K_2HPO_4$ | 2.9 |
| $Na_2S.9H_2O$ | 0.5 |
| Nitritrilotriacetic acid | 0.015 |
| $FeSO_4.7H_2O$ | 0.001 |
| $MnCl_2.4H_2O$ | 0.001 |
| $CoCl_2.6H_2O$ | 0.0060 |
| $CaCl_2.2H_2O$ | 0.001 |
| $ZnCl_2$ | 0.001 |
| $CuCl_2$ | 0.0002 |
| $H_3BO_3$ | 0.0001 |
| Na molybdate | 0.0001 |
| $Na_2SeO_3$ | 0.0001 |
| $NiSO_4.6H_2O$ | 0.002 |
| Biotin | 0.00001 |
| Folic acid | 0.00001 |
| Pyridoxine HCl | 0.0005 |
| Thiamine HCl | 0.0005 |
| Riboflavin | 0.0003 |
| Niacin | 0.0003 |
| Panothenic acid | 0.0003 |
| P—aminobenzoic acid | 0.0003 |
| Lipoic acid | 0.0003 |
| Methanol | — 10 mM |

A biologically pure culture was prepared by inoculating the media with a pure strain of *M. barkeri* MS and cells were grown under a $N_2/CO_2$ (95:5) gas phase in the absence of light at a temperature of 37° C. for about 168 hours.

The vitamin $B_{12}$-activity substances, corrinoids, were assayed by the modification of the plate method of Harrison, Lees, and Wood described by Krzycki and Zeikus in Quantification of Corrinoids in methanogenic bacteria. Current Microbiology 3:243–245 (1980). Cell samples were prepared for analysis by washing three times in 100 mM phosphate buffer, pH 7. The cell paste was dried for at least 12 h. at 60° C. than extracted in 1.3% $Na_2HPO_4.7H_2O$, 1.2% citric acid.$H_2O$ and 1.3% $Na_2S_2O_5$. A ratio of 10 mg. dry cells to 1.0 ml of extracting solution was employed. The extracts were autoclaved at 121° C., 15 psi, for 15 minutes to liberate any cell-bound coorinoids, then centrifuged. The supernatant was diluted to 1:10 or 1:100 prior to assay in order to prevent bisulfite toxicity to the assay organism.

The results of the assay are reported in Table 1.

EXAMPLE 2

Methanosarcina barkeri Growth on Acetate

The process of Example 1 was repeated except that the M. barkeri was grown in an acetate complex medium that contained 0.1% NH$_4$Cl, 0.04% K$_2$HPO$_4$, 0.1% MgCL$_2$, 0.2% yeast extract, 0.2% Trypticase, 1.0% sodium acetate, 0.0001% resazurin, 0.05% cysteine HCl and 0.01% Na$_2$S under an N$_2$/CO$_2$ (95:5) gas phase. The corrinoid content was assayed as before and the results are reported in Table 1.

EXAMPLE 3

Methanosarcina barkeri Growth on H$_2$/CO$_2$

The process of Example 1 was repeated employing ad the assimilable carbon source a mixture of H$_2$/CO$_2$ in place of the methanol. The results also are reported in Table 1.

EXAMPLE 4

Butyribacterium methylotrophicum Growth on Methanol

A biologically pure culture was prepared containing the Marburg strain ATCC 33266 in a medium of the following composition.

| Component | Amount/L |
|---|---|
| Double distilled H$_2$O | 945 ml |
| MgCl.6H$_2$O | 0.2 g |
| CaCl$_2$.2H$_2$O | 0.1 g |
| NH$_4$Cl | 7.0 g |
| $^a$Trace mineral sln. #2 | 10 ml |
| $^b$Vitamin sln. | 5 ml |
| Resazurin solution (0.2%) | 1 ml |
| Yeast extract | 7.0 g |
| Sodium acetate | 4.1 g |
| Methanol | 5 ml (125 mM/l) |
| Na$_2$S (2.5%) | 20 ml |

| a | (g/l) | b | (g/l) |
|---|---|---|---|
| Nitriloacetic acid | 12.8 | Biotin | .002 |
| FeSO$_4$.7H$_2$O | 0.1 | Folic acid | .002 |
| MnCl$_2$.4H$_2$O | 0.1 | B$_6$HCl | .01 |
| COCl$_2$.6H$_2$O | 0.17 | B$_1$HCl | .005 |
| CaCl$_2$.2H$_2$O | 0.1 | B$_2$ | .005 |
| ZnCl$_2$ | 0.1 | Niacin | .005 |
| CuCl$_2$ | 0.02 | Pantothenic acid | .005 |
| H$_3$BO$_4$ | 0.01 | B$_{12}$ | .0001 |
| NaCl | 1.0 | PaBA | .005 |
| Na$_2$SeO$_3$ | 0.017 | Lipoic Acid | .005 |
| NiSO$_4$.6H$_2$O | 0.026 | | |

An anaerobic fermentation was conducted under a N$_2$/CO$_2$ (95:5) gas phase at 37° C. for three days.

Vitamin B$_{12}$ levels were measured at 7.4 mg/g cells on a cell yield basis. The cells were found to contain more than 1% of Vitamin B$_{12}$ on a dry weight basis. Corrinoids in cells were quantified by the bioassay utilizing Escherichia coli previously described.

TABLE 1

Organism
Methanosarcina barkeri strain MS

| Energy source: | nmoles corrinoid/mg cell dry weight |
|---|---|
| Acetate | 1.6 ± 0.7 |
| MeOH | 4.1 ± 0.95 |
| H$_2$/CO$_2$ | 2.5 ± 0.6 |

Results of Escherichia coli bioassay. All organisms were in mineral medium without B$_{12}$, except complex medium was used to grow M. barkeri on acetate. ±Values represent standard deviations.

B. methylotrophicum appears to be an excellent agent for vitamin synthesis in that it has a high growth rate, produces potentially useful fermentative end-products, is resistant to lysis and is anaerobic.

Anaerobic fermentation processes have significant advantages over aerobic processes in that the mono-cultures and more easily maintained, and oxygenation is unnecessary.

It will be apparent to those skilled in the art that the foregoing description has been for purposes of illustration and that a number of modifications and changes can be made without departing from the spirit and scope of the invention. For example, for larger scale production the B$_{12}$-activity substance producing organisms can be grown in commercial size fermentators and the cells separated by centrifugation or other conventional techniques. In addition, while specific species of the producing organisms have been described, those species are liable, as are microorganisms generally, to undergo variations and mutations, either spontaneously or under the influence of a mutagen. Thus, the many variants of the strain which are obtainable by irradiation with X-rays, gamma rays, ultra-violet light, etc., by monocel isolation, by culture on media containing various chemicals, or by any other mutagenic treatment, as well as the mutants spontaneously derived from the strain, which produce the desired products and grow upon single carbon products should not be considered to represent any other distinct species and may be utilized for the purposes of this invention.

In view of the foregoing, the invention is to be limited only by the following claims.

We claim:

1. The process for producing vitamin B$_{12}$-active substances which comprises cultivating a vitamin B$_{12}$-active substance producing microorganism selected from the species of Methanosarcina barkeri DSM D800 and Butyribacterium methylotrophicum ATCC 33266 under anaerobic conditions in a culture medium containing methanol as the main source of assimilable carbon, a source of assimilable nitrogen, essential minerals, growth factors and cobalt ions and then recovering the vitamin B$_{12}$-active substances from the culture broth.

2. The process of claim 1 in which the microorganism is Methanosarcina barkeri DSM D800.

3. The process of claim 2 in which the fermentation is conducted in the absence of light.

4. The process of claim 1 in which the microorganism is Butyribacterium methylotrophicum ATCC 33266.

5. The process of claim 1 in which the fermentation is conducted under a N$_2$/CO$_2$ atmosphere.

6. A biologically pure culture comprising a microorganism identified as Methanosarcina barkeri DSM D800 and a nutrient medium consisting essentially of methanol as the primary source of assimilable carbon, an assimilable source of nitrogen and essential mineral salts, including cobalt ions, said culture being capable of producing vitamin B$_{12}$-active substances in recoverable quantity upon anaerobic fermentation.

7. A biologically pure culture comprising a microorganism identified as Butyribacterium methylotrophicum ATC 33266 and a nutrient medium consisting essentially of methanol as the primary source of assimilable carbon, an assimilable nitrogen source and essential growth factors and minerals, including cobalt ions, said culture being capable of producing vitamin B$_{12}$-activity substances in recoverable quantity upon anaerobic fermentation.

8. The culture of claim 7 which contains a growth stimulating amount of sodium acetate.

9. The culture of claim 7 which contains as a growth factor yeast extract.

* * * * *